US008026097B2

(12) United States Patent
Campana et al.

(10) Patent No.: US 8,026,097 B2
(45) Date of Patent: *Sep. 27, 2011

(54) EXPANSION OF NK CELLS AND THERAPEUTIC USES THEREOF

(75) Inventors: Dario Campana, Germantown, TN (US); Chihaya Imai, Niigata (JP)

(73) Assignee: St. Jude Children's Research Hospital, Memphis, TN (US)

( * ) Notice: Subject to any disclaimer, the term of this patent is extended or adjusted under 35 U.S.C. 154(b) by 240 days.

This patent is subject to a terminal disclaimer.

(21) Appl. No.: 12/206,204

(22) Filed: Sep. 8, 2008

(65) Prior Publication Data
US 2009/0011498 A1    Jan. 8, 2009

Related U.S. Application Data

(63) Continuation of application No. 11/074,525, filed on Mar. 8, 2005, now Pat. No. 7,435,596, which is a continuation-in-part of application No. 10/981,352, filed on Nov. 4, 2004, now abandoned.

(51) Int. Cl.
C12N 5/16 (2006.01)
(52) U.S. Cl. ...................................... 435/455
(58) Field of Classification Search .................. None
See application file for complete search history.

(56) References Cited

U.S. PATENT DOCUMENTS

| 5,359,046 | A | 10/1994 | Capon |
| 5,674,704 | A | 10/1997 | Goodwin |
| 5,686,281 | A | 11/1997 | Roberts |
| 6,103,521 | A | 8/2000 | Capon |
| 6,303,121 | B1 | 10/2001 | Kwon |
| 7,070,995 | B2 | 7/2006 | Jensen |
| 7,435,596 | B2 * | 10/2008 | Campana et al. ............. 435/455 |
| 2003/0147869 | A1 | 8/2003 | Riley |

OTHER PUBLICATIONS

Alderson, M.R.; et al., "Molecular and Biological Characterization of Human 4-1BB and its Ligand," Eur. J. Immunol., 1994, pp. 2219-2227, vol. 24.
Brentjens, R.J., et al., "Eradication of Systemic B-Cell Tumors by Genetically Targeted Human T Lymphocytes Co-Stimulated B Cd80 and Interleukin-15," Nature Medicine, 2003, pp. 279-286, vol. 9.
Bukczynski, J, et al., "Costimulation of Human CD28—T Cells by 4-1BB Ligand," Eur. J. Immunol., 2003, pp. 446-454, vol. 33.
Burkett, P.R., et al., "Coordinate expression and trans presentation of interleukin (IL<)-15Ra and IL-15 supports natural killer cell and memory CD8+T Cell Homeostasis", J. Exp. Med, 200:825-834 (2004).

Campana, D., et al., "Immunophenotyping of Leukemia,"Jour of Immunol Methods, 2000, pp. 59-75, vol. 243.
Carson, W.E., et al., A potential role for Interleukin-15 in the regulation of human natural killer cell survival, J. Clin. Invest., 99:937-943 (1997).
Cheung, N-K. V., et al., "Anti-Idiotypic Antibody Facilitates scFv Chimeric Immune Receptor-Gene Transduction and Clonal expansion of Human Lymphocytes for Tumor Therapy," Hybridoma and Hybridomics, 2003, pp. 209-218, vol. 22(4).
Cooper, L.J., et al., "T-Cell Clones can be Rendered Specific for CD19: Toward the Selective Augmentation Of the Graft-Versus-B-Lineage Leukemia Effect," Blood, 2003, pp. 1637-1644, vol. 101.
Cooper, M.A., et al., In vivo evidence for a dependence on interleukin 15 for survival of natural killer cells, Blood, 100:3633-3638 (2002).
DeBenedette, MA, et al., "Costimulatin of CD28—T Lymphocytes by 4-1BB Ligand," J. Immunol., 1997, pp. 551-559, vol. 158.
Eshhar, Z, et al., "Functional Expression of Chimeric Receptor Genes in Human T Cells," J. Immunol. Methods, 2001, pp. 67-76, vol. 248.
Farag, S.S., et al., "Natural killer cell receptors: new biology and insights into the Graft-versus-leukemia effect", Blood, 100:1935-1947 (2002).
Fehniger, T.A., et al., "Ontogeny and Expansion of Human Natural Killer Cells: Clinical Implications," Int Rev Immunol, 2001, pp. 503-534, vol. 20.
Finney, H.M, et al., "Activation of Resting Human Primary T Cells with Chimeric Receptors: Constimulation from CD28, Inducible Constimulator, CD134, and CD137 in Series with Signals from TCR Chain,"Journ of Immun, 2004, pp. 104-113, vol. 172.
Geiger, T.L., et al., "Integrated src Kinase and Costimulatory Activity Enhances Signal Transduction through Single-Chain Chimeric Receptors in T Lymphocytes," Blood, 2001, pp. 2364-2371, vol. 98.
Goodwin, R.G., et al., "Molecular Cloning of a Ligand for the Inducible T Cell Gene 4-1BB: A Member of an Emerging Family of Cytokines with Homology to Tumor Necrosis Factor", Eur. J. Immunol., 1993, pp. 2631-2641, vol. 23.
Greenwald, et al., Annu. Rev. Immunol., 2005, 23:515-548.
Harada, H., et al., "A Wilms Tumor Cell Line, HFWT, can Greatly Stimulate Proliferation of CD56+ Human Natural Killer Cells and their Novel Precursors in Blood Mononuclear Cells," Exp. Hematology, 2004, pp. 614-621, vol. 32.
Harada, H., et al., "Selective Expansion of Human Natural Killer Cells from Peripheral Blood Mononuclear Cells B the Cell Line, HFWT," Jpn. J. Cancer Res., 2002, pp. 313-319, vol. 93.
Haynes, N.M., et al., "Single-Chain Antigen Recognition Receptors that Costimulate Potent Rejection of Established Experimental Tumors," Blood, 2002, pp. 3155-3163, vol. 100.
Haynes, N.M., et al., "Rejection of Syngeneic Colon Carcinoma by CTLs Expressing Single-chain Antibody Receptors Codeliverin CD28 Costimulation,"J Immunol, 2002, pp. 5780-5786, vol. 169.

(Continued)

Primary Examiner — Ilia Ouspenski
(74) Attorney, Agent, or Firm — Alston & Bird LLP

(57) ABSTRACT

The present invention relates to novel methods for preferentially activating and expanding NK cells. The methods utilize the stimulatory effects of IL-15 and CD137 ligand to preferentially expand and activate NK cells in a mixed cell culture comprising NK cells.

3 Claims, No Drawings

OTHER PUBLICATIONS

Hombach, A., et al., "Tumor-Specific T Cell Activation by Recombinant Immunoreceptors: CD3ζ Signaling and CD28 Costimulation are Simultaneously Required for Efficient IL-2 Secretion and can be Integrated into One Combined CD28/CD3ζ Signaling Receptor Molecule"; *J. Immunol*, 2001, pp. 6123-6131, vol. 167.

Hurtado, J.C., et al., "Signals Through 4-1BB are Costimulatory to Previously Activated Splenic T Cells and Inhibit Activation-Inducted Cell Death," *J. Immunol.*, 1997, pp. 2600-2609, vol. 158.

Imai, C., et al., "A novel method for propagating primary natural killer (NK) cells allows highly efficient expression of anti-CD19 chimeric receptors and generation of powerful cytotoxicity against NK-resistant acute lymphoblastic leukemia cells", Abtract #306, B*lood* 104 (Nov. 16, 2004).

Kim, Y-J., et al., "Human 4-1BB Regulates CD28 Co-Stimulation to Promote Th1 Cell Responses," *Eur. J. Immunol.*, 1998, pp. 881-890, vol. 28.

Ishiwata et al., *Exp. Pathol.*, 1991, 41:1-9, Abstract (1 page).

Kim, Y-J., et al., "Novel T Cell Antigen 4-1BB Associates with the Protein Tyrosine Kinase p56$^{lck1}$," *J Immunol*, 1993, pp. 1255-1262, vol. 151.

Klein, E., et al., "Properties of the K562 Cell Fine, Derived from a Patient with Chronic Myeloid Leukemia," *Int. J. Cancer*, 1976, pp. 421-431, vol. 18.

Klingemann, H-G., et al., "Ex Vivo Expansion of Natural Killer Cells for Clinical Applications," *Cytotherapy*, 2004, pp. 15-22, vol. 6.

Kwon, B.S., et al., "cDNA Sequences of Two Inducible T-Cell Genes," *Proc Natl Acad Sci*, 1989, pp. 1963-1967, vol. 86.

Li, Q., et al., "Polarization Effects of 4-1BB During CD28 Costimulation in Generating Tumor-Reactive T Cells for Cancer Immunotherapy," *Cancer Res*, 2003, pp. 2546-2552, vol. 63.

Lozzio, C.B., et al., "Human Chronic Myelogenous Leukemia Cell-Line with Positive Philadelphia Chromosome," *Blood*, 1975, pp. 321-334, vol. 45.

Maher, J., et al., "Human T-lymphocyte Cytoxicity and Proliferation Directed by a Single Chimeric TCRzeta/CD28 Receptor," *Nat Biotechnol*, 2002, pp. 70-75, vol. 20.

Martinet, O., et al., "Cell Activation with Systemic Agonistic Antibody Versus Local 4-1BB Ligand Gene Delivery Combined with Interieukin-12 Eradicate Liver Metases of Breast Cancer," *Gene Ther*, 2002, pp. 786-792, vol. 9.

Maus, M.V., et al., "Ex vivo expansion of polyclonal and antigen-specific cytotoxic T lymphocytes by artificial APCs expressing ligands for the T-cell receptor, CD28 and 4-1BB", *Nat Biotechnology*, 20:143-148 (2002).

May, K.F. Jr., et al., "Anti-4-168 Monoclonal antibody enhances rejection of large tumor burden by Promoting survival but notclonal expansion of tumor-specific CD8+ T cells," *Cancer Res*, 2002, pp. 3459-3465, vol. 62.

Melero, I., et al., "Amplification of Tumor Immunity by GeneTransfer of the Co-Stimulatory 4-1BB Ligand: Synergy with the CD28 Co-Stimulatory Pathway," *Eur J. Immunol*, 1998, pp. 1116-1121, vol. 28.

Melero, I., et al., "Monoclonal Antibodies Against the 4-1BB T-Cell Activation Molecule Eradicate Established Tumors," *Nat Medicine*, 1997, pp. 682-685, vol. 3.

Merero, I., et al., "NK1.1 cells express 4-1BB (CDw 137) constimulatory molecule and are required for tumor immunity elicited by anti-4-1BB monoclonal antibodies", *Cell Immun*, 190:167-172 (1998).

Moretta, L., et al., "Unravelling natural killer cell function: triggering and inhibitory human NK receptors", *EMBO* 23:255-259 (2004).

Nicholson, I.C., et al., "Construction and Characterization of a Functional CD19 Specific Single Chain Fv Fragment for Immunotherapy of B Lineage Leukemia and Lymphoma" Mol Immunol, 1997, pp. 1157-1165, vol. 34.

Oelke, M., et al., "Ex vivo induction and expansion of antigen-specific cytotoxic T cells by HLA-lg-coated artificial antigen-presenting cells"; *Nature Medicine* 9:619-624 (2003).

Pollok, K.E., et al., "Inducible T Cell Antigen 4-1BB," J Immunol, 1993, pp. 771-781, vol. 150.

Riley et al., *Blood*, 2005, 105:13-21.

Robertson, M.J., et al., "Costimulation of human natural killer cell proliferation: role of accessory cytokines and cell contact-dependent signals", *Nat Immune* 15:213-226 (1996).

Shuford, W.W., et al., "4-1BB Costimulatory Signals Preferentially Induce CD8+ T Cell Proliferation and Lead to the Amplification In Vivo of Cytotoxic T Cell Responses," *J Exp Mod*, 1997, pp. 47-55, vol. 186.

Takahashi, C., et al., "Cutting Edge: 4-1BB is a Bona Fide CD8 T Cell Survival Signal," *J Immunol*, 1999, pp. 5037-5040, vol. 162.

Vinay, D.S., and B.S. Kwon, "Role of 4-1BB in Immune Responses," *Immunology*, 1988, pp. 481-489, vol. 10.

Zeis, M. et al., "Aliogenic MHC-Mismatched Activated Natural Killer Cells Administered After Bone Marrow Transplantation Provide a Strong Graft-Versus-Leukemia Effect in Mice," *Br J Haematol*, 1997, pp. 757-761, vol. 96.

ATCC No. CCL-243, 1975.

U.S. Appl. No. 11/074,525 Office Action, Mar. 23, 2007, Campana.
U.S. Appl. No. 11/074,525 Response to Office Action, Jun. 25, 2007, Campana.
U.S. Appl. No. 11/074,525 Office Action, Sep. 18, 2007, Campana.
U.S. Appl. No. 11/074,525 Response to Office Action, Dec. 7, 2007, Campana.
U.S. Appl. No. 11/074,525 Office Action, Jan. 3, 2008, Campana.
U.S. Appl. No. 11/074,525 Response to Office Action, Apr. 1, 2008, Campana.

* cited by examiner

EXPANSION OF NK CELLS AND THERAPEUTIC USES THEREOF

CROSS-REFERENCE TO RELATED APPLICATIONS

This application is a continuation of U.S. patent application Ser. No. 11/074,525, filed on Mar. 8, 2005 which was a continuation in part of U.S. patent application Ser. No. 10/981,352 filed Nov. 4, 2004.

GOVERNMENT INTEREST

This invention was made in part with U.S. Government support under National Institutes of Health grant no. CA 58297. The U.S. Government may have certain rights in this invention.

FIELD OF THE INVENTION

This invention relates to activation and expansion of cells for therapeutic uses, in particular for activations and expansion of NK cells for chimeric receptor-based cell therapy.

BACKGROUND

B-cell malignancies of children and adults, such as acute lymphoblastic leukemia (ALL), chronic lymphocytic leukemia (CLL) and non-Hodgkin lymphoma (NHL), are often incurable with intensive chemotherapy. For many patients, bone marrow ablation followed by allogeneic hematopoietic stem cell transplantation is the only potentially curative option, but the disease may return after transplant [Pui C H, Campana D, Evans W E. Childhood acute lymphoblastic leukemia—Current status and future perspectives. Lancet Oncology 2:597-607 (2001)]. The well-documented association between T-cell-mediated graft-versus-host disease (GvHD) and a delay or suppression of leukemic relapse after allogeneic stem cell transplantation, has led some investigators to manipulate GvHD by infusion of donor T lymphocytes. Although this procedure can induce a measurable antineoplastic response [Porter D L, et al., Induction of graft-versus-host disease as immunotherapy for relapsed chronic myeloid leukemia. N Engl J Med 330:100106 (1994); Kolb H J, et al., Graft-versus-leukemia effect of donor lymphocyte transfusions in marrow grafted patients. European Group for Blood and Marrow Transplantation Working Party Chronic Leukemia. Blood 86:2041-2050 (1995); Slavin S, et al., Allogeneic cell therapy with donor peripheral blood cells and recombinant human interleukin-2 to treat leukemia relapse after allogeneic bone marrow transplantation. Blood 87:2195-2204 (1996); Collins R H, Jr., et al., Donor leukocyte infusions in 140 patients with relapsed malignancy after allogeneic bone marrow transplantation. J Clin Oncol 15:433-444 (1997)], it carries the risk of severe GvHD, particularly in those patients (>70%) who lack an HLA-identical donor. Moreover, in some B-cell malignancies such as ALL, the effect of lymphocyte infusions is often inadequate [Kolb H J, et al., Graft-versus-leukemia effect of donor lymphocyte transfusions in marrow grafted patients. European Group for Blood and Marrow Transplantation Working Party Chronic Leukemia. Blood 86:2041-2050 (1995); Verdonck L F, et al., Donor leukocyte infusions for recurrent hematologic malignancies after allogeneic bone marrow transplantation: impact of infused and residual donor T cells. Bone Marrow Transplant 22:1057-1063 (1998); Collins R H, Jr., et al., Donor leukocyte infusions in acute lymphocytic leukemia. Bone Marrow Transplant 26:511-516 (2000)].

In addition to T cell immune responses, natural killer (NK) cells exert cytotoxicity against cancer cells and appear to be clinically relevant [Schroers R, et al. Gene transfer into human T lymphocytes and natural killer cells by Ad5/F35 chimeric adenoviral vectors. Exp Hematol; 32:536-546 (2004)]. While T cells recognize tumor associated peptide antigen expressed on surface HLA class I or class II molecules, antigen nonspecific immune responses are mediated by NK cells that are activated by the failure to recognize cognate "self" HLA class I molecules. The graft-versus-tumor effect of transplants using HLA matched donors is mediated by antigen specific T cells, while transplantation using HLA mismatched donors can also lead to donor NK cells with potent antitumor activity. HLA mismatched haplo-identical transplants can exert a powerful anti-leukemia effect based on expansion of antigen nonspecific donor NK cells.

Recent studies have emphasized the potential of NK-cell therapy in recipients of allogeneic hematopoietic stem cell transplantation. In animal models of transplantation, donor NK cells could lyse leukemic cells and host lympho-hematopoietic cells without affecting nonhematopoietic tissues, [Caligiuri M A, Velardi A, Scheinberg D A, Borrello I M. Immunotherapeutic approaches for hematologic malignancies. Hematology; Am Soc Hematol Educ Program 337-353 (2004)] suggesting that NK-mediated graft-versus-leukemia responses may occur in the absence of systemic disease. Because NK cells are inhibited by self-HLA molecules which bind to killer immunoglobulin-like receptors (KIR), these findings have led to the clinical practice of selecting hematopoietic stem cell transplant donors with an HLA and KIR type that favors NK-cell activation and thus could be expected to promote an antileukemic effect [Sadelain M, Riviere I, Brentjens R. Targeting tumours with genetically enhanced T lymphocytes. Nat Rev Cancer 3:35-45 (2003); Cooper L J, Topp M S, Serrano L M, et al. T-cell clones can be rendered specific for CD19: toward the selective augmentation of the graft-versus-B-lineage leukemia effect. Blood 101:1637-1644 (2003); Brentjens R J, Latouche J B, Santos E, et al. Eradication of systemic B-cell tumors by genetically targeted human T lymphocytes co-stimulated by CD80 and interleukin-15. Nat Med 9:279-286 (2003)]. However, selection of the "best" donor is limited to patients who have more than one potential donor and the capacity of NK cells to lyse lymphoid cells is generally low and difficult to predict. [Sadelain M, Riviere 1, Brentjens R. Targeting tumours with genetically enhanced T lymphocytes. Nat Rev Cancer 3:35-45 (2003); Brentjens R J, Latouche J B, Santos E, et al. Eradication of systemic B-cell tumors by genetically targeted human T lymphocytes co-stimulated by CD80 and interleukin-15. Nat Med 9:279-286 (2003); Imai C, Mihara K, Andreansky M, Nicholson I C, Pui C H, Campana D. Chimeric receptors with 4-1BB signaling capacity provoke potent cytotoxicity against acute lymphoblastic leukemia. Leukemia 18:676-684 (2004); Ito C, Kumagai M, Manabe A, et al. Hyperdiploid acute lymphoblastic leukemia with 51 to 65 chromosomes: A distinct biological entity with a marked propensity to undergo apoptosis. Blood 93:315-320 (1999)].

The established methods for cell expansion favor T cell expansion and even after T cells are depleted, residual T cells typically become prominent after stimulation. Methods for the expansion of T lymphocytes have been described in US published patent applications, #20030147869, #20030224520, 20040101519 and #20040110290. Immunotherapy with NK cells has been limited by the inability to obtain sufficient numbers of pure NK cells suitable for manipulation and expansion. Thus there is a need for better methods to preferentially expand NK cells from a population of NK cells and T cells.

SUMMARY OF THE INVENTION

The present invention is based on the concept that expression of chimeric receptors on NK cells could overcome HLA-mediated inhibitory signals, thus endowing the cells with cytotoxicity against otherwise NK-resistant cells. The invention provides a novel method that allows specific and vigorous preferential expansion of NK cells lacking T-cell receptors (CD56$^+$ CD3$^-$ cells) and their highly efficient transduction with chimeric receptors.

The present invention provides a method for obtaining an enriched NK cell population suitable for transduction with a chimeric receptor. This method comprises the preferential expansion of NK cells within a mixed population of NK cells and T cells by co-culturing the mixed population of cells with a cell line that activates NK cells and not T lymphocytes. This NK activating cell line is composed of cells that (a) lack or poorly express major histocompatibility complex I molecules, (b) express membrane bound interleukin-15 and a co-stimulatory factor ligand, (c) activate natural killer cells, and (d) fail to activate T lymphocytes. In a particular embodiment the NK activating cell line is the K562 myeloid leukemia cell line or the Wilms tumor cell line HFWT. In another embodiment of the invention the co-stimulatory factor ligand is CD137L.

Another aspect of the invention provides a method of preferentially expanding natural killer (NK) cells in a mixed cell culture comprising NK cells and T lymphocytes which comprises culturing said mixed cell culture with interleukin-15 receptor antibodies and CD137 ligand antibodies coupled to a solid support.

DETAILED DESCRIPTION OF THE INVENTION

Definitions 4-1BB ligand (CD137L) is claimed and described in U.S. Pat. No. 5,674,704. 4-1BB receptor is expressed on several antigen-presenting cells such as macrophages and activated B cells [Pollok et al., J. Immunol. 150:771 (1993) Schwarz et al., Blood 85:1043 (1995)). The interaction of 4-1BB and its ligand provides a co-stimulatory signal leading to T cell activation and growth [Goodwin et al., Eur. J. Immunol. 23:2631 (1993); Alderson et al., Eur. J. Immunol. 24:2219 (1994); Hurtado et al., J. Immunol. 155:3360 (1995); Pollock et al., Eur. J. Immunol. 25:488 (1995); DeBenedette et al., J. Exp. Med. 181:985 (1995)]. These observations suggest an important role for 4-1BB in the regulation of T cell-mediated immune responses [Ignacio et al., Nature Med. 3:682 (1997)].

The term IL-15 (interleukin 15) refers to a cytokine that stimulates NK cells [Fehniger T A, Caligiuri M A. Blood 97(1):14-32 (2001)]. It has become apparent that IL-15 presented through cell to cell contact has a higher NK stimulating activity than soluble IL-15 [Dubois S, et al., Immunity 17(5): 537-547 (2002); Kobayashi H, et al., Blood (2004) PMID: 15367431; Koka R, et al., J Immunol 173(6):3594-3598 (2004); Burkett P R, et al., J Exp Med 200(7):825-834 (2004)]. To express membrane-bound IL-15 a construct consisting of human IL-15 mature peptide (NM 172174) was fused to the signal peptide and transmembrane domain of human CD8α.

A solid support means any surface capable of having an agent attached thereto and includes, without limitation, metals, glass, plastics, polymers, particles, microparticles, co-polymers, colloids, lipids, lipid bilayers, cell surfaces and the like. Essentially any surface that is capable of retaining an agent bound or attached thereto. A prototypical example of a solid support used herein, is a particle such as a bead.

The term "substantially free of means a population of cells, e.g. NK cells, that is at least 50% free of non-NK cells, or in certain embodiments at least 60, 70, 80, 85, or 90% free of non-NK cells.

A "co-stimulatory signal" refers to a signal, which in combination with a primary signal, such as TCR/CD3 ligation, leads to NK cell proliferation and/or upregulation or down-regulation of key molecules.

To specifically or preferentially expand NK cells means to culture a mixed population of cells that contains a small number of NK cells so that the NK cells proliferate to numbers greater than other cell types in the population.

To activate T cells and NK cells means to induce a change in their biologic state by which the cells express activation markers, produce cytokines, proliferate and/or become cytotoxic to target cells. All these changes can be produced by primary stimulatory signals. Co-stimulatory signals amplify the magnitude of the primary signals and suppress cell death following initial stimulation resulting in a more durable activation state and thus a higher cytotoxic capacity.

DESCRIPTION OF THE INVENTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes [-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Haines & S. J. Higgins eds. (1985)]; "Transcription And Translation" [B. D. Haines & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984); CURRENT PROTOCOLS IN IMMUNOLOGY Q. E. Coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein are hereby incorporated herein by reference.

Obtaining an enriched population of NK cells for use in therapy has been difficult to achieve. Specific NK cell expansion has been problematic to achieve with established methods, where CD3$^+$ T cells preferentially expand. Even after T cell depletion, residual T cells typically become prominent after stimulation. However, in accordance with the teachings of the present invention NK cells may be preferentially expanded by exposure to cells that lack or poorly express major histocompatibility complex I and/or II molecules and which have been genetically modified to express membrane bound IL-15 and 4-1BB ligand (CDI37L). Such cell lines include, but are not necessarily limited to, K562 [ATCC, CCL 243; Lozzio et al., Blood 45(3): 321-334 (1975); Klein et al., Int. J. Cancer 18: 421-431 (1976)], and the Wilms tumor cell line HFWT. [Fehniger T A, Caligiuri M A. Int Rev Immunol 20(3-4):503-534 (2001); Harada H, et al., Exp Hematol 32(7):614-621 (2004)], the uterine endometrium tumor cell line HHUA, the melanoma cell line HMV-II, the hepatoblastoma cell line HuH-6, the lung small cell carcinoma cell lines Lu-130 and Lu-134-A, the neutoblastoma cell lines NB 19 and N1369, the embryonal carcinoma cell line from testis NEC 14, the cervix carcinoma cell line TCO-2, and the bone marrow-metastated neuroblastoma cell line TNB 1 [Harada H., et al., Jpn. J. Cancer Res 93: 313-319 (2002)]. Preferably the cell line used lacks or poorly expresses both MHC I and II molecules, such as the K562 and HFWT cell lines.

A solid support may be used instead of a cell line. Such supports will have attached on its surface at least one molecule capable of binding to NK cells and inducing a primary activation event and/or a proliferative response or capable of binding a molecule having such an affect thereby acting as a scaffold. The support may have attached to its surface the CD137 ligand protein, a CD137 antibody, the IL-15 protein or an IL-15 receptor antibody. Preferably, the support will have IL-15 receptor antibody and CD137 antibody bound on its surface.

The invention is intended to include the use of fragments, mutants, or variants (e.g., modified forms) of the IL-15 and/or CD137 ligand proteins or antigens that retain the ability to induce stimulation and proliferation of NK cells. A "form of the protein" is intended to mean a protein that shares a significant homology with the IL-15 or CD137 ligand proteins or antigen and is capable of effecting stimulation and proliferation of NK cells. The terms "biologically active" or "biologically active form of the protein," as used herein, are meant to include forms of the proteins or antigens that are capable of effecting enhanced activated NK cell proliferation. One skilled in the art can select such forms based on their ability to enhance NK cell activation and proliferation upon introduction of a nucleic acid encoding said proteins into a cell line. The ability of a specific form of the IL-15 or CD137 ligand protein or antigen to enhance NK cell proliferation can be readily determined, for example, by measuring cell proliferation or effector function by any known assay or method.

Antigen-specific cells can be expanded in vitro for use in adoptive cellular immunotherapy in which infusions of such cells have been shown to have anti-tumor reactivity in a tumor-bearing host. The compositions and methods of this invention can be used to generate a population of NK cells that deliver both primary and co-stimulatory signals for use in immunotherapy in the treatment of cancer, in particular the treatment of lung cancer, melanoma, breast cancer, prostate cancer, colon cancer, renal cell carcinoma, ovarian cancer, neuroblastoma, rhabdomyosarcoma, leukemia and lymphoma. The compositions and methods described in the present invention may be utilized in conjunction with other types of therapy for cancer, such as chemotherapy, surgery, radiation, gene therapy, and so forth.

Expansion of NK Cells

The present invention shows that human primary NK cells may be expanded in the presence of a myeloid cell line that has been genetically modified to express membrane bound IL-15 and 4-1BB ligand (CD137L). A cell line modified in this way which does not have MHC class I and II molecules is highly susceptible to NK cell lysis and activates NK cells.

For example, K562 myeloid cells can be transduced with a chimeric protein construct consisting of human IL-15 mature peptide fused to the signal peptide and transmembrane domain of human CD8α and GFP. Transduced cells can then be single-cell cloned by limiting dilution and a clone with the highest GFP expression and surface IL-15 selected. This clone can then be transduced with human CD137L, creating a K562-mb15-137L cell line.

To preferentially expand NK cells, peripheral blood mononuclear cell cultures containing NK cells are cultured with a K562-mbl5-137L cell line in the presence of 10 IU/mL of IL-2 for a period of time sufficient to activate and enrich for a population of NK cells. This period can range from 2 to 20 days, preferably about 5 days. Expanded NK cells may then be further modified if desired before therapeutic or other use.

Administration of Activated NK Cells

Methods of re-introducing cellular components are known in the art and include procedures such as those exemplified in U.S. Pat. Nos. 4,844,893 and 4,690,915. The amount of activated NK cells used can vary between in vitro and in vivo uses, as well as with the amount and type of the target cells. The amount administered will also vary depending on the condition of the patient and should be determined by considering all appropriate factors by the practitioner.

Example 1

Artificial Antigen Producing Cells (APCs) Pave the Way for Clinical Application by Potent Primary In Vitro Induction Materials and Methods Cells The CD 19 human B-lineage ALL cell lines RS4;11, OP-1, 380, 697, and KOPN57bi; the T-cell line GEM-C7; and the myeloid cell lines K562 and U-937 were available in our laboratory. Cells were maintained in RPMI-1640 (Gibco, Grand Island, N.Y.) supplemented with 10% fetal calf serum (FCS; BioWhittaker, Walkersville, Md.) and antibiotics.

Primary leukemia cells were obtained with appropriate informed consent and Institutional Review Board (M) approval from nine patients with B-lineage ALL; from four of these patients, we also studied (with IRB approval) cryopreserved peripheral blood samples obtained during clinical remission. An unequivocal diagnosis of B-lineage ALL was established by morphologic, cytochemical, and immunophenotypic criteria; in each case, more than 95% of the cells were positive for CD19. Peripheral blood was obtained from eight healthy adult donors. Mononuclear cells collected from the samples by centrifugation on a Lymphoprep density step (Nycomed, Oslo, Norway) were washed twice in phosphate-buffered saline (PBS) and once in AIM-V medium (Gibco).

Plasmids and Retrovirus Production

The anti-CD 19-ζ, anti-CD 19-BB-i and anti-CD 19-truncated (control) plasmids are described in Imai, C, et al., Leukemia 18:676-684 (2004). The pMSCV-IRES-GFP, pEQ-PAM3(-E), and pRDF constructs were obtained from the St. Jude Vector Development and Production Shared Resource. The intracellular domains of human DAP 10, 4-1BB ligand and interleukin-15 (IL-15) with long signal peptide were subcloned by polymerase chain reaction (PCR) with a human spleen cDNA library (from Dr. G. Neale, St. Jude Children's Research Hospital) used as a template. An antiCD 19-DAP 10 plasmid was constructed by replacing the intracellular domain of anti-CD 19-ζ with that of DAP 10, using the SOE-PCR (splicing by overlapping extension by PCR) method. The signal peptide of CD8 cc, the mature peptide of IL-15 and the transmembrane domain of CDBα were assembled by SOE-PCR to encode a "membrane-bound" form of IL-15. The resulting expression cassettes were subcloned into EcoRI and XhoI sites of MSCV-IRES-GFP.

The RD114-pseudotyped retrovirus was generated as described in Imai, C, et al., Leukemia 18:676-684 (2004). We used calcium phosphate DNA precipitation to transfect 293T cells with anti-CD19-ζ, anti-CD19DAP 10, anti-CD19-BB-~, or anti-CD19-truncated; pEQ-PAM3(-E); and pRDF. Conditioned medium containing retrovirus was harvested at 48 hours and 72 hours after transfection, immediately frozen in dry ice, and stored at −80° C. until use.

Development of K562 Derivatives, Expansion of NK Cells and Gene Transduction

K562 cells were transduced with the construct encoding the "membrane-bound" form of IL-15. Cells were cloned by limiting dilution, and a single-cell clone with high expression of GFP and of surface IL-15 ("K562-mb15") was expanded. This clone was subsequently transduced with human 4-1BB ligand and designated as "K562-mb15-41BBL". K562 cells expressing wild-type IL-15 ("K562-wt15") or 4-IBBL ("K562-41BBL") were produced by a similar procedure. Peripheral blood mononuclear cells ($1.5 \times 10^6$) were incubated in a 24-well tissue culture plate with or without $10^6$ K562-derivative stimulator cells in the presence of 10 N/mL human IL-2 (National Cancer Institute BRB Preclinical Repository, Rockville, Md.) in RPMI-1640 and 10% FCS. Mononuclear cells stimulated with K562-mb15-41BBL were transduced with retroviruses, as previously described for T cells [Melero I, et al., NK1.1 cells express 4-iBB (CDwl37) costimulatory molecule and are required for tumor immunity elicited by anti-4-1BB monoclonal antibodies. Cell Immunol 190:167-172 (1998)]. Briefly, 14-mL polypropylene centrifuge tubes (Falcon) were coated with human fibronectin (100 μg/mL; Sigma, St. Louis, Mo.) or RetroNectin (50 μg/mL; TaKaRa, Otsu, Japan). Prestimulated cells ($2 \times 10^5$) were resuspended in the tubes in 2-3 mL of virus-conditioned medium with polybrene (4 μg/mL; Sigma) and centrifuged at 2400×g for 2 hours (centrifugation was omitted when RetroNectin was used). The multiplicity of infection (4 to 6) was identical in each experiment comparing the activity of different chimeric receptors. After centrifugation, cells were left undisturbed for 24 hours in a humidified incubator at 37° C., 5% $CO_2$. The transduction procedure was repeated on two successive days. After a second transduction, the cells were re-stimulated with K562-mb 15-4 1BBL in the presence of 10 IU/mL of IL-2. Cells were maintained in RPMI-1640, 10% FCS, and 10 IU/mL IL-2.

Detection of Chimeric Receptor Expression and Immunophenotyping

Transduced NK cells were stained with goat anti-mouse (Fab)$_2$ polyclonal antibody conjugated with biotin (Jackson Immunoresearch, West Grove, Pa.) followed by streptavidin conjugated to peridinin chlorophyll protein (PerCP; Becton Dickinson, San Jose, Calif.). For Western blotting, cells were lysed in RIPA buffer (PBS, 1% Triton-X100, 0.5% sodium deoxycholate, 0.1% SDS) containing 3 μg/mL of pepstatin, 3 μg/mL of leupeptin, 1 mM of PMSF, 2 mM of EDTA, and 5 μg/mL of aprotinin. Centrifuged lysate supernatants were boiled with an equal volume of loading buffer with or without 0.1 M DTT, and then separated by SDS PAGE on a precast 10-20% gradient acrylamide gel (BioRad, Hercules, Calif.). The proteins were transferred to a PVDF membrane, which was incubated with primary mouse anti-human CD3ζ monoclonal antibody (clone 8D3; Pharmingen). Membranes were then washed, incubated with a goat anti-mouse IgG horseradish peroxidase-conjugated second antibody, and developed by using the ECP kit (Pharmacia, Piscataway, N.J.).

The following antibodies were used for immunophenotypic characterization of expanded and transduced cells: anti-CD3 conjugated to fluorescein isothiocyanate (FITC), to peridinin chlorophyll protein (PerCP) or to energy-coupled dye (ECD); anti-CD 10 conjugated to phycoerythrin (PE); anti-CD19 PE; anti-CD22 PE; anti-CD56 FITC, PE or allophycocyanin (AFC); anti-CD 16 CyChrome (antibodies from Becton Dickinson; Pharmingen, San Diego; or Beckman-Coulter, Miami, Fla.); and anti-CD25 PE (Dako, Carpinteria, Calif.). Surface expression of KIR and NK activation molecules was determined with specific antibodies conjugated to FIX or PE (from Beckman-Coulter or Becton-Dickinson), as previously described [Brentjens R J, Latouche J B, Santos E, et al. Eradication of systemic B-cell tumors by genetically targeted human T lymphocytes co-stimulated by CD80 and interleukin-15. Nat Med 9:279-286 (2003)]. Antibody staining was detected with a FACScan or a LSR II flow cytomete (Becton Dickinson).

Cytotoxicity Assays and Cytokine Production

Target cells ($1.5 \times 10^5$) were placed in 96-well U-bottomed tissue culture plates (Costar, Cambridge, Na) and incubated with primary NK cells transduced with chimeric receptors at various effector:target (E:T) ratios in RPMI-1640 supplemented with 10% FCS; NK cells were cultured with 1000 U/mL IL-2 for 48 hours before the assay. Cultures were performed in the absence of exogenous IL-2. After 4 hours and 24 hours, cells were harvested, labeled with CD10 PE or CD22 PE and CD56 FITC, and assayed by flow cytometry as previously described. The numbers of target cells recovered from cultures without NK cells were used as a reference.

For cytokine production, primary NK cells ($2 \times 10^5$ in 200 μl) expressing chimeric receptors were stimulated with various target cells at a 1:1 ratio for 24 hours. The levels of IFN-γ and GM-CSF in cell-free culture supernatants were determined with a Bio-Plex assay (BioRad).

Statistical Analysis

A test of equality of mean NK expansion with various stimuli was performed using analysis of variance for a randomized complete block design with each donor considered a random block. Tukey's honest significant difference procedure was used to compute simultaneous confidence intervals for each pairwise comparison of the differences of treatment means. Differences in cytotoxicities and cytokine production among NK cells bearing different chimeric receptors were analyzed by the paired Student's t test.

Results

Culture Conditions that Favor the Expansion of Primary NK Cells

To transduce chimeric receptors into primary NK cells, we searched for stimuli that would induce specific NK cell proliferation. In preliminary experiments, peripheral blood mononuclear cells of CD3$^+$ T lymphocytes were depleted and the remaining cells were stimulated with IL-2 (1000 U/mL) or IL-15 (10 ng/mL). Under these culture conditions there was no expansion of NK cells, which in fact progressively declined in numbers. With PHA (7 mg/mL) and IL-2 (1000 U/mL) as stimuli, we observed a 2- to 5-fold expansion of CD56$^+$ CD3$^-$ NK cells after 1 week of culture. However, despite the low proportion of contaminating CD3$^+$ cells (<2% in two experiments) at the beginning of the cultures, these cells expanded more than NK cells (>30-fold expansion), and after 1 week of culture represented approximately 35% of the cell population.

NK cells can be stimulated by contact with the human leukemia cell line K562, which lacks HLA-antigen expression, [Robertson M J, Cameron C, Lazo S, Cochran K J, Voss S D, Ritz J. Costimulation of human natural killer cell proliferation: role of accessory cytokines and cell contact-dependent signals. Nat Immun 15:213-226 (1996)] and genetically modified K562 cells have been used to stimulate cytotoxic T lymphocytes [Maus M V, Thomas A K, Leonard D G, et al. Ex vivo expansion of polyclonal and antigen-specific cytotoxic T lymphocytes by artificial APCs expressing ligands for the T-cell receptor, CD28 and 4-1BB. Nat Biotechnol 20:143-148 (2002)]. We tested whether the NK-stimulatory capacity of K562 cells could be increased through enforced expression of additional NK-stimulatory molecules, using two molecules that are not expressed by K562 cells and are known to stimulate NK cells. One molecule, the ligand for 4-1BB (4-1BBL), triggers activation signals after binding to 4-1BB (CD 137), a signaling molecule expressed on the surface of NK cells [Melero I, Johnston J V, Shufford W W, Mittler R S, Chen L. NK1.I cells express 4-IBB (CDw137) costimulatory molecule and are required for tumor immunity elicited by anti-4-IBB monoclonal antibodies. Cell Immunol 190:167-172 (1998)]. The other molecule, IL-15, is a cytokine known to promote NK-cell development and the survival of mature NK cells [Carson W E, Fehniger T A, Haldar S, et al. A potential role for interleukin-15 in the regulation of human natural killer cell survival J Clin Invest. 99:937-943 (1997); Cooper M A, Bush J E, Fehniger T A, et al. In vivo evidence for a dependence on interleukin 15 for survival of natural killer cells. Blood 100:3633-3638 (2002); Fehniger T A, Caligiuri M A. Ontogeny and expansion of human natural killer cells: clinical implications. Int Rev Immunol 20:503-534 (2001); Wu J, Lanier L L. Natural killer cells and cancer. Adv Cancer Res 90:127-56:127-156 (2003)]. Since IL-15 has greater biological activity when presented to NK cells bound to IL-15Rα on the cell membrane of stimulatory cells, rather than in its soluble form, we made a construct containing the human IL-15 gene fused to the gene encoding the human CD8α, transmembrane domain, and used it to transduce K562 cells. Expression of IL-15 on the surface of K562 cells was more than five times higher with the IL-15-CD8α construct than with wild-type IL-15.

To test whether the modified K562 cells expressing both 4-11313L and IL-I5 (K562 mbl5-41BBL cells) promote NK cell expansion, we cultured peripheral blood mononuclear cells from seven donors in the presence of low-dose (10 U/mL) IL-2 as well as irradiated K562 cells transduced with 4-1 BBL and/or IL-15, or with an empty control vector. Expression of either 4-1 BBL or IL-15 by K562 cells improved the stimulation of NK-stimulatory capacity of K562 in some cases but not overall, whereas simultaneous expression of both molecules led to a consistent and striking amplification of NK cells (median recovery of CD56$^+$ CD3$^-$ cells at 1 week of culture, 2030% of input cells [range, 1020%-2520%] compared with a median recovery of 250% [range, 150%-640%] for K562 cells lacking 4-1BBL and IL-15; P<0.0001). In 24 experiments with cells from 8 donors, NK-cell expansion after 3 weeks of culture with K562 cells expressing both stimulatory molecules ranged from 309-fold to 12,409 fold (median, 1089-fold). Neither the modified nor unmodified K562 cells caused an expansion of T lymphocytes. Among expanded CD56$^+$ CD3$^-$ NK cells, expression of CD56 was higher than that of unstimulated cells; expression of CD 16 was similar to that seen on unstimulated NK cells (median CD16$^+$ NK cells in 7 donors: 89% before expansion and 84% after expansion). We also compared the expression of KIR molecules on the expanded NK cells with that on NK cells before culture, using the monoclonal antibodies CD158a (against KIR 2DL1), CD158b (2□L2), NKBI (3DL1) and NKAT2 (2DL3). The prevalence of NK subsets expressing these molecules after expansion resembled that of their counterparts before culture, although the level of expression of KIR molecules was higher after culture. Similar results were obtained for the inhibitory receptor CD94, while expression of the activating receptors NKp30 and NKp44 became detectable on most cells after culture. In sum, the immunophenotype of expanded NK cells reiterated that of activated NK cells, indicating that contact with K562-mb1541BBL cells had stimulated expansion of all subsets of NK cells.

Transduction of NK Cells with Chimeric Receptors

Before transducing peripheral blood mononuclear cells with retroviral vectors containing chimeric receptor constructs and GFP, we stimulated them with K562-mb15-41BBL cells. In 27 experiments, the median percentage of NK cells that were GFP$^+$ at 7-11 days after transduction was 69% (43%-93%). Chimeric receptors were expressed at high levels on the surface of NK cells and, by Western blotting, were in both monomeric and dimeric configurations.

To identify the specific signals required to stimulate NK cells with chimeric receptors, and overcome inhibitory signals mediated by KIR molecules and other NK inhibitory receptors that bind to HLA class I molecules, we first compared two types of chimeric receptors containing different signaling domains: CD3ζ, a signal-transducing molecule containing three immunoreceptor tyrosine-based activation motifs (ITAMs) and linked to several activating receptors expressed on the surface of NK cells [Farag S S, Fehniger T A, Ruggeri L, Velardi A, Caligiuri M A. Natural killer cell receptors: new biology and insights into the graft-versus-leukemia effect. Blood 100:1935-1947 (2002); Moretta L, Moretta A. Unravelling natural killer cell function: triggering and inhibitory human NK receptors. EMBO J 23:255-259 (2004)], and DAP 10, a signal transducing molecule with no ITAMs linked to the activating receptor NKG2D and previously shown to trigger NK cytotoxicity [Farag S S, Fehniger T A, Ruggeri L, Velardi A, Caligiuri M A. Natural killer cell receptors: new biology and insights into the graft-versus-leukemia effect. Blood 100:1935-1947 (2002); Moretta L, Moretta A. Unravelling natural killer cell function: triggering and inhibitory human NK receptors. EMBO J 23:255-259 (2004); Billadeau D D, Upshaw J L, Schoon R A, Dick C J, Leibson P J. NKG2D-DAPIO triggers human NK cell-mediated killing via a Syk-independent regulatory pathway. Nat. Immuno. 4:557-564 (2003)]. As a control, we used NK cells transduced with a vector containing an antiCD19 receptor but no signaling molecules or containing GFP alone.

NK cells were challenged with the CD19$^+$ leukemic cell lines 380, 697 and RS4;11, all of which express high levels of HLA-class I molecules by antibody staining. By genotyping, RS4;11 is Cw4/Cw3, Bw4 and A3; 380 is Cw4/Cw4, Bw4; and 697 is Cw3/Cw3. Hence, these cell lines were fully capable of inhibiting NK cell cytotoxicity via binding to NK inhibitory receptors.

Expression of receptors without signaling molecules did not increase NK-mediated cytotoxicity over that exerted by NK cells transduced with the vector containing only GFP. By contrast, expression of anti-CD 19-ζ receptors markedly enhanced NK cytotoxicity in all experiments, regardless of the intrinsic ability of donor NK cells to kill leukemic targets. For example, 380 cells were highly resistant to NK cells from donors 2 and 3, but were killed when these donor cells expressed anti-CD 19-ζ receptors. Similar observations were made for RS4; 11 cells and the NK cells of donor 1 and for 697 cells and NK cells of donor 2. Moreover, the anti-CD 19-ζ receptors led to improved killing of target cells even when natural cytotoxicity was present. In all experiments, the cytotoxicity triggered by the anti-CD 19-ζ receptor was enhanced over that achieved by replacing CD3ζ with DAP 10 (P<0.001).

4-1BB-Mediated Costimulatory Signals Enhance NK Cytotoxicity

Previous studies have shown that the addition of costimulatory molecules to chimeric receptors enhances the proliferation and cytotoxicity of T lymphocytes [Imai C, Mihara K, Andreansky M, Nicholson I C, Pui C H, Campana D. Chimeric receptors with 4-1BB signaling capacity provoke potent cytotoxicity against acute lymphoblastic leukemia. Leukemia 18:676-684 (2004)]. Of the two best known costimulatory molecules in T lymphocytes, CD28 and 4-1BB, only 4-1BB is expressed by NK cells [Melero I, Johnston J V, Shufford W W, Mittler R S, Chen L. NKLI cells express 4-1BB (CDwl37) costimulatory molecule and are required for tumor immunity elicited by anti-4-1BB monoclonal antibodies. Cell Immunol 1998; 190:167-172 (1998); Lang S, Vujanovic N L, Wollenberg B, Whiteside T L. Absence of B7.1-CD28/CTLA-4-mediated co-stimulation in human NK cells. Eur J Immunol 28:780-786 (1998); Goodier M R, Londei M. CD28 is not directly involved in the response of human CD3CD56+ natural killer cells to lipopolysaccharide: a role for T cells. Immunology 111:384-390 (2004)]. We determined whether the addition of 4-1 BB to the anti-CD 19-ζ receptor would enhance NK cytotoxicity. In a 4 hour-cytotoxicity assay, cells expressing the 41BB-augmented receptor showed a markedly better ability to kill CD 19⁺ cells than did cells lacking this modification. The superiority of NK cells bearing the anti-CD 19-BB-ζ receptor was also evident in 24-hour assays with NK cells from different donors cultured at a 1:1 ratio with the leukemia cell lines 697, KOPN57bi and OP-1.

Next, we determined whether the antileukemic activity of NK cells expressing antiCD19-BB-ζ receptors extended to primary leukemic samples. In five samples from children with different molecular species of ALL, NK cells expressing the 4-1BB receptors exerted strong cytotoxicity that was evident even at low E:T ratios (e.g., <1:1; FIG. 7) and uniformly exceeded the activity of NK cells expressing signaling receptors that lacked 4-1 BB. Even when donor NK cells had natural cytotoxicity against ALL cells and CD3ζ receptor did not improve it, addition of 4-1BB to the receptor significantly enhanced cytotoxicity. Consistent with their increased cytotoxicity, NK cells expressing anti-CD 19-BB-z mediated more vigorous activation signals. Forty-six percent of NK cells bearing this receptor expressed the IL2 receptor a chain CD25 after 24 hours of coculture with CD19⁺ ALL cells, compared with only 17% of cells expressing the anti-CD19-ζ receptor and <1% for cells expressing receptors that lacked stimulatory capacity. Moreover, anti-CD 19-BB-C receptors induced a much higher production of IFN-g and GM-CSF upon contact with CD19+ cells than did receptors without 41BB.

We asked whether the expression of signaling chimeric receptors would affect spontaneous NK activity against NK-sensitive cell lines not expressing CD 19. Spontaneous cytotoxicity of NK cells from three donors against the CD 19⁻ leukemia cell lines K562, U937 and CEM-C7 was not diminished by expression of chimeric receptors, with or without 4-1BB.

Anti-CD 19 Chimeric Receptors Induce NK Cytotoxicity Against Autologous Leukemic Cells To determine whether the NK cell expansion and transduction system that we developed would be applicable to clinical samples, we studied peripheral blood samples that had been obtained (and cryopreserved) from four patients with childhood B-lineage ALL in clinical remission, 25-56 weeks from diagnosis. NK cell expansion occur in all four samples: recovery of after one week of culture with K562-mbl5-41BBL cells, recovery of CD56⁺ CD3⁻ NK cells ranged from 1350% to 3680% of the input.

After transduction with chimeric receptors, we tested the cytotoxicity of the NK cells against autologous leukemic lymphoblasts obtained at diagnosis. Expression of anti-CD 19-BB-ζ receptors overcame NK cell resistance of autologous cells; NK cells expressing the receptors exerted cytotoxicity which was as powerful as that observed with allogeneic targets.

DISCUSSION

In this study, we demonstrated that the resistance of cancer cells to NK cell activity can be overcome by chimeric receptors expressed on primary NK cells. The stimulatory signals triggered by the receptors upon contact with target cells predominated over inhibitory signals and induced powerful cytotoxicity against NK-resistant leukemic cell lines and primary leukemic cells. We found that the type of stimulatory signal delivered by the chimeric receptor was a key factor in inducing cytotoxicity. Although DAP 10 signaling can elicit NK cytotoxicity, chimeric receptors containing this molecule in our study induced weaker NK cell activity than that generated by CD3ζ-containing receptors, despite identical levels of surface expression. We also found that addition of the costimulatory molecule 4-1BB to the chimeric receptors markedly augmented cytotoxicity, and that receptors containing both CD3ζ and 4-1BB triggered a much more robust NK cell activation and cytokine production than did those containing only CD3ζ.

The important contribution of 4-1 BB signals agrees with findings that anti-4-I BB antibodies activate murine NK cells [Pan P Y, et al., Regulation of dendritic cell function by NK cells: mechanisms underlying the synergism in the combination therapy of IL-12 and 4-1BB activation. J Immunol 172: 4779-4789 (2004)], and enhance their anti-tumor activity. Leukemic lymphoid cells usually do not express 4-1BB ligand: only 2 of 284 diagnostic B-lineage ALL samples studied by gene arrays at our institution expressed 4-I BB ligand transcripts [Yeoh E J, et al., Classification, subtype discovery, and prediction of outcome in pediatric acute lymphoblastic leukemia by gene expression profiling. Cancer Cell 1: 133-143 (2002)]. Hence, 4-1BB signals can be delivered to NK cells only if the molecule is incorporated into the receptor.

Efficient and stable transduction of primary NK cells is notoriously difficult, prompting us to devise a new gene transduction method for the present study. Most investigators have demonstrated efficient gene transfer only in continuously growing NK cell lines [Roberts M R, et al., Antigen-specific cytolysis by neutrophils and NK cells expressing chimeric immune receptors bearing zeta or gamma signaling domains. J. Immunol. 161:375-384 (1998); Nagashima S, et al., Stable transduction of the interleukin-2 gene into human natural killer cell lines and their phenotypic and functional characterization in vitro and in vivo. Blood 91:3850-3861 (1998)] or reported methods yielding only transient gene expression [Billadeau D D, et al., NKG2D-DAP 10 triggers human NK cell-mediated killing via a Syk-independent regulatory pathway. Nat. Immuno. 4:557-564 (2003); Trompeter H I, et al., Rapid and highly efficient gene transfer into natural killer cells by nucleofection. J Immunol Methods 274:245-256 (2003); Schroers R, et al., Gene transfer into human T lymphocytes and natural killer cells by Ad5/F35 chimeric adenoviral vectors. Exp Hematol 32:536-546 (2004)]. We achieved stable expression of chimeric receptors in primary CD56⁺ CD3⁻ NK cells by using an RD114-pseudotyped retroviral vector and specifically expanding primary CD56+ CD3− NK cells before they were exposed to the retrovirus, a step that allowed highly efficient gene expression. Although several cytokines such as IL-2, IL-12 and IL-15 have been reported to stimulate NK cells [Carson W E, et al., A potential role for interleukin-15 in the regulation of human natural killer cell survival J Clin Invest. 99:937-943 (1997); Trinchieri G, et al., Response of resting human peripheral blood natural killer cells to interleukin 2. J Exp Med 1984; 160: 1147-1169 (1984); Naume B, et al., A comparative study of IL-12 (cytotoxic lymphocyte maturation factor)-, IL-2-, and IL-7-induced effects on immunomagnetically purified CD56+ NK cells. J Immunol 148:2429-2436 (1992)], their capacity to induce proliferation of resting CD56+ CD3 cells has been poor, unless accessory cells are present in the cultures. Perussia et al. Nat Immun Cell Growth Regul 6:171-188 (1987), found that contact with irradiated B-lymphoblastoid cells induced as high as a 25-fold expansion of NK cells after 2 weeks of stimulation, while Miller et al. Blood; 80:2221-2229 (1992) reported an approximate 30-fold expansion of NK cells after 18 days of culture with 1000 U/mL IL-2 and monocytes. However, these culture conditions are likely to promote the growth of CD3+ T lymphocytes as well as NK cells. Since our ultimate aim is to generate pure preparations for out donor NK cells devoid of CD3+ T lymphocytes, that can be infused into recipients of allogeneic hematopoietic stem cell transplants, we searched for methods that would maximize NK cell expansion without producing T-cell mitogenicity.

Contact with K562 cells (which lack MHC-class I molecule expression and hence do not trigger KIR-mediated inhibitory signals in NK cells) is known to augment NK cell proliferation in response to IL-15. We found that membrane-bound IL-15 and 4-1BBL, coexpressed by K562 cells, acted synergistically to augment K562-specific NK stimulatory capacity, resulting in vigorous expansion of peripheral blood CD56+ CD3− NK cells without concomitant growth of T lymphocytes. After 2-3 weeks of culture, we observed NK cell expansions of up to 10,000-fold, and virtually pure populations of NK cells could be obtained, even without the need for T-cell depletion in some cases. NK cells expanded in this system retained the immunophenotypic diversity seen among peripheral blood subsets of NK cells, as well as their natural cytotoxicity against sensitive target cells, even after transduction with different chimeric receptors. Hence, this system should help studies of NK cell biology which require specific cell expansion and/or gene transduction, but it should also be adaptable to clinical applications after generating K562 mb 15-4 1 BBL cells that comply with current good manufacturing practices for clinical trials. Recently, Harada et al. reported that expansions of CD56+ CD3− cells (up to 400-fold after 2 weeks) were apparently superior after contact with another HLA class I-negative cell line, the Wilms tumor cell line HFWT [Harada H, Saijo K, Watanabe S, et al. Selective expansion of human natural killer cells from peripheral blood mononuclear cells by the cell line, HFWT. Jpn J Cancer Res 93:313 (2002)]. Future studies should determine whether HFWT cells express 41BBL or whether enforced expression of 4-1BBL together with IL-15 results in a greater specific expansion of NK cells than seen with modified K562 cells.

In the context of allogeneic hematopoietic stem cell transplantation, infusions of activated donor T cells would carry an unacceptably high risk of severe GvHD, particularly in recipients of haploidentical or mismatched transplants. By contrast, infusions of pure CD56 CD3 NK cells should not impose that risk [Ruggeri L, et al., Effectiveness of donor natural killer cell alloreactivity in mismatched hematopoietic transplants. Science 295 :2097-2100 (2002)]. Most clinical studies of the therapeutic effects of NK cells have been performed in an autologous setting and have yielded only moderately promising results [Farag S S, et al., Natural killer cell receptors: new biology and insights into the graft-versus-leukemia effect. Blood 100:1935-1947 (2002); Chiorean E G, Miller J S. The biology of natural killer cells and implications for therapy of human disease. J Hematother Stem Cell Res 10:451-463 (2001)]. This is not surprising because NK cell activity is inhibited by surface receptors that recognize autologous HLA molecules expressed by both normal and neoplastic cells. Allogeneic NK cells may be more effective, but even in an allogeneic setting the capacity of NK cells to kill malignant lymphoid cells is generally modest and often negligible [Caligiuri M A, Velardi A, Scheinberg D A, Borrello I M. Immunotherapeutic approaches for hematologic malignancies. Hematology (Am Soc Hematol Educ Program) 337-353 (2004)]. Leung et al. [J Immunol 172:644-650 (2004)] detected NK cytotoxicity against an ALL cell line expressing particularly low levels of inhibitory HLA molecules, but cytotoxicity was much lower than that observed against the NK-cell target K562: only about 50% of the ALL cells were killed at an effector:target ratio of 40:1. In that study, RS4;11 cells, which express HLA-C alleles that bind the most commonly expressed KIRs, were NK-resistant, whereas these cells, as well as autologous leukemic cells, were highly sensitive to NK cells expressing anti-CD 19 signaling receptors in our study. NK cells expressing signaling chimeric receptors have much more powerful antileukemic activity than unmodified NK cells, and can kill target cells irrespective of their HLA profile. An increased understanding of the signals leading to immune cell activation, together with progress in gene cloning and transfer, have made the treatment of cancer with "adoptively acquired immunity" a realistic goal. Clinical precedents, such as administration of T-cell clones that target cytomegalovirus epitopes [Walter E A, et al., Reconstitution of cellular immunity against cytomegalovirus in recipients of allogeneic bone marrow by transfer of T-cell clones from the donor. N Engl J Med 1995; 333:1038-1044 (1995)] or EBV-specific antigens [Rooney C M, et al., Use of gene-modified virus-specific T lymphocytes to control Epstein-Barr-virus-related lymphoproliferation. Lancet 345:9-13 (1995)], attest to the clinical feasibility of adoptive immune cell therapy. Nonetheless, there are potential limitations that may affect the effectiveness of cell therapy guided by chimeric receptors. One is that the murine scFv portion of the chimeric receptor or the fusion sites of the human regions that compose it may trigger a host immune response leading to elimination of the modified cells [Sadelain M, et al., Targeting tumours with genetically enhanced T lymphocytes. Nat Rev Cancer 3:35-45 (2003)]. Although the impact of such an event in a clinical setting remains to be determined, we anticipate that immune responses against modified NK cells will be limited in immune-suppressed patients after hematopoietic stem cell transplantation. Another potential limitation is that adoptively transferred cells may have inadequate persistence in vivo, although a recent study showed that NK cells obtained from haploidentical donors and activated ex vivo could expand in patients when infused after administration of high-dose cyclophosphamide and fludarabine, which caused an increased in endogenous IL-15 [Miller J S, et al., Successful adoptive transfer and in vivo expansion of human haploidentical NK cells in cancer patients. Blood; in press (2005)]. We speculate that such expansions would also occur with genetically-modified NK cells, and suggest that further studies to identify signaling molecules that promote NK cell proliferation when incorporated into chimeric receptors are warranted. In patients at a high risk of leukemia or lymphoma relapse, the expected benefits of genetically-modified NK cells will outweigh the risk of insertional oncogenesis posed by the use of retroviruses for chimeric receptor transduction [Baum C, et al., Side effects of retroviral gene transfer into hematopoietic stem cells. Blood 101:2099-2114 (2003)]. We also predict that the coexpression of suicide genes will become a useful safety measure in clinical studies [Marktel S, et al., Immunologic potential of donor lymphocytes expressing a suicide gene for early immune reconstitution after hematopoietic T-cell-depleted stem cell transplantation. Blood 101: 1290-1298 (2003)]; this strategy would also ensure that the elimination of normal CD 19$^+$ B-lineage cells is only temporary.

Novel therapies that bypass cellular mechanisms of drug resistance are urgently needed for patients with refractory leukemia and lymphoma. NK cell alloreactivity is a powerful new tool for improving the therapeutic potential of allogeneic hematopoietic stem cell transplantation. The results of this study indicate that signaling receptors can enhance the efficacy of NK cell alloreactivity and widen its applicability. We envisage initial clinical trials in which donor NK cells, collected by apheresis, are expanded ex vivo as described here, transduced with chimeric receptors and then infused after transplantation in patients with B-lineage ALL. The target molecule for the chimeric receptors, CD19, was selected because it is one of the most widely expressed surface antigens among B-cell malignancies, including ALL, CLL and NHL. In these malignancies, CD19 is highly expressed on the surface of virtually all cells but has limited or no expression in normal tissues [Campana D, Behm F G. Immunophenotyping of leukemia. J Immunol Methods 243:59-75 (2000)]. However, the NK-cell strategy of immunotherapy we describe would not have to be directed to the CD 19 antigen, but could be applied to any of the numerous molecules identified as potential targets for chimeric receptor-based cell therapy in cancer patients.

All of the above U.S. patents, U.S. patent application publications, U.S. patent applications, foreign patents, foreign patent applications and non-patent publications referred to in this specification, including but not limited to U.S. patent application Ser. No. 09/960,264, filed Sep. 20, 2001; which is a continuation-in-part of U.S. application Ser. No. 10/981, 352, filed Nov. 4, 2004 are incorporated herein by reference, in their entirety. All of references, patents, patent applications, etc. cited above, are incorporated herein in their entirety.

The invention claimed is:

1. A modified cell line comprising cells that lack major histocompatibility complex I molecules wherein said cells are genetically modified to express membrane bound interleukin-15 and a co-stimulatory factor ligand CD137L, where said modified cell line activates natural killer (NK) cells and fails to activate T lymphocytes.

2. The cell line of claim 1, wherein said cells also lack major histocompatibility complex II molecules.

3. A method of preferentially expanding natural killer (NK) cells in a mixed cell culture comprising NK cells and T lymphocytes which comprises culturing said mixed cell culture with a modified cell line comprising cells that lack major histocompatibility complex I molecules wherein said cells are genetically modified to express membrane bound interleukin-15 and a co-stimulatory factor ligand CD137L, where said modified cell line activates natural killer (NK) cells and fails to activate T lymphocytes.

* * * * *